United States Patent [19]

Zhao

[11] Patent Number: 5,833,686
[45] Date of Patent: Nov. 10, 1998

[54] ULTRA-HIGH-FREQUENCY COSMETIC APPARATUS

[76] Inventor: Xinhua Zhao, Xinsi Road, Baqiao, Xian, Shaanxi Province 710038, China

[21] Appl. No.: 793,676

[22] PCT Filed: Sep. 1, 1994

[86] PCT No.: PCT/CN94/00069

§ 371 Date: May 28, 1997

§ 102(e) Date: May 28, 1997

[87] PCT Pub. No.: WO96/06575

PCT Pub. Date: Jul. 3, 1996

[51] Int. Cl.$^6$ ..................................................... A61B 17/39
[52] U.S. Cl. ................................................. 606/34; 606/37
[58] Field of Search ..................... 606/34, 37, 36

[56] References Cited

U.S. PATENT DOCUMENTS 3,699,967 10/1972 Anderson .
4,473,075 9/1984 Pexroth .

FOREIGN PATENT DOCUMENTS

| 2055028 | 3/0000 | China | ............................ | A61B 17/39 |
| 2066720 | 12/1990 | China | ............................ | A61B 17/39 |
| 1067805 | 1/1993 | China | ............................ | A61B 17/39 |
| 1070327 | 3/1993 | China | ............................ | A61B 17/39 |
| 1099255 | 3/1995 | China | ............................ | A61B 17/39 |

*Primary Examiner*—John P. Lacyk
*Assistant Examiner*—Roy D. Gibson
*Attorney, Agent, or Firm*—Fulbright & Jaworski, LLP

[57] ABSTRACT

An ultra-high-frequency (UHF) cosmetic apparatus using UHF electric current of about 50 MHz to treat 80 kinds of dermatosis without any side effect, e.g. to remove a variety of benign vegetations on skin, especially on facial skin. The apparatus can also be used to perforate on ear lobes, to radically treat hicismus and hairiness. The UHF oscillating signal source of the invention consists of an UHF oscillator, a power amplifier, a coupling isolating circuit and an electric current-frequency stabilizing circuit, the UHF signal is output to the area to be treated through an output electrode and a variety of scapels of needle-type or of blade type. After treatment by the apparatus, the skin is smooth without any scar and infection, and the restoration period is very short. The apparatus is suitable for use in medical beauty treatment.

20 Claims, 2 Drawing Sheets

ULTRA-HIGH-FREQUENCY COSMETIC APPARATUS

FIELD OF THE INVENTION

The present invention relates to a surgical cosmetic apparatus for removing a variety of benign skin growths, especially on facial skin, eradicating underarm odor and unwanted hair once for all, recovering kinds of scars as well as making ear holes for earring by use of UHF electric current of about 50 MHz without any side effect on the human body, and pertains to the field of skin-beauty surgery.

BACKGROUND OF THE INVENTION

Conventional skin-beauty technique comprises such cosmetic treatments as cryotherapy, laser, erosion with Chinese traditional and modern medicines, skin polishing and the use of high frequency electric blade (mainly for surgical incision and stopping bleeding in operation). But there are following drawbacks in the use of the above-mentioned treatments: (1) contamination of the surgical wound surface, unsatisfactory evaporation of the inflicted tissues, and stickiness of the inflicted tissues; (2) the size and depth of the surgical treatment area being difficult to control, scars remaining after operation, relapse rate being high and the skin surface after treatment being rough. Several ultra-high-frequency cosmetic apparatuses have been proposed to overcome the above-mentioned drawbacks. A particular structure of this kind of cosmetic apparatus is disclosed in Chinese patent application No. 91104006 entitled "ultra-high-frequency cosmetic apparatus". However, it has the disadvantages of employing the commercially available "five sense organs treatment device" as the ultra-high-frequency signal source, which fails to provide, the required precision of the parameters of frequencies, stability indices, and safeguard when the naked metallic electrodes are directly applied on the human body.

It is therefore an object of the present invention to provide an improvement of the above-mentioned cosmetic apparatus, in which the ultra-high-frequency signal source outputs stable ultra-high-frequency signals with high precision parameters that enables the safe application of the naked metallic electrodes directly on human body.

SUMMARY OF THE INVENTION

The present invention provides an ultra-high-frequency cosmetic apparatus comprising an ultra-high-frequency signal source, output electrodes and a variety of surgical treatment appliances in the forms of needle and blade, characterized in that the ultra-high-frequency signal source is constituted by the following circuits: a tunable oscillating circuit for generating ultra-high-frequency oscillating signals; a power amplifying circuit connecting with an output intensity adjustment and display circuit, the input of the power amplifying circuit being connected to the output of the tunable oscillating circuit, a current and frequency stabilizing circuit having its input connected to the output of the power amplifying circuit and its output connected to the tunable oscillating circuit, a coupling isolating circuit having its input connected to the output of the power amplifying circuit and its output connected to the output electrodes and the variety of surgical treatment appliances; and a power supply circuit for providing electrical power to the circuits, the circuit connecting with a voltage adjustment and display circuit.

Preferably, the output signal of the apparatus has a frequency of 40–58 MHz and an intensity of 0–180 mA.

Preferably, the output signal of said ultra-high-frequency cosmetic apparatus has a frequency of 50 MHz.

Preferably, the ultra-high-frequency oscillating circuit uses FU-7 electronic tubes and an LC self-excited oscillating circuit.

Preferably, the power amplifying circuit employs a push-pull power amplifying circuit consisting of a pair of FU-7 tubes.

Preferably, the coupling isolating circuit employs two capacitors having resistance to voltage of more than 1 KV as isolating elements.

Preferably, the ultra-high-frequency cosmetic apparatus is provided with an air cooler.

The present invention also provides an ultra-high-frequency signal source, output electrodes and a variety of surgical treatment appliances in the forms of needle and blade, characterized in that said ultra-high-frequency signal source is constituted by the following circuits: a tunable oscillating and power amplifying circuit for generating ultra-high-frequency oscillating signals, the circuit connecting with an output intensity adjustment and display circuit and using a plurality of electronic tubes, a coupling isolating circuit having its input connected to the output of said tunable oscillating and power amplifying circuit and its output connected to said output electrodes and said variety of surgical treatment appliance; a power supply circuit for providing 600 V as anode voltage of said electronic tube, 8.3 V as filament voltage of said electronic tube, the circuit connecting with a voltage adjustment and display circuit, and a current and frequency stabilizing circuit having its input connected to the output of 8.3 V of said power supply circuit and its output connected to the filaments of the electronic tubes of said tunable oscillating and power amplifying circuit; and the output signal of the apparatus has a frequency of 50–58 MHz and an intensity of 0–180 mA.

With the stable ultra-high-frequency signals output by the signal source described above in combination with different types of output electrodes, the cosmetic apparatus according to the present invention has no side effect on human body, the inflicted tissues can be evaporated completely, the surgical surface is fresh and clean, and layered treatments can be realized. By the addition of the method for operating from the circumference towards the center of the inflicted area, the regrowth of the surgical surface can be made flat, the surface of the polished skin can be made flat and smooth. In addition, these electrodes driven by such ultra-high-frequency signals have the effects of dephlogistication, stopping bleeding and detumescence. Clinical data indicate that the average cure rate by the use of the ultra-high-frequency cosmetic apparatus according to the present invention is 99.28%, and for a skilled doctor, the cure rates can be up to 100%.

The various features of novelty which characterizes the invention are pointed out with particularity in the claims annexed to and forming a part of this specification. For a better understanding of the invention, its operating advantages and specific objects obtained by its use, reference should be had to the accompanying drawings and descriptive matter in which there is illustrated and described a preferred embodiment of the invention.

DESCRIPTION OF PREFERRED EMBODIMENT

Figure 1:
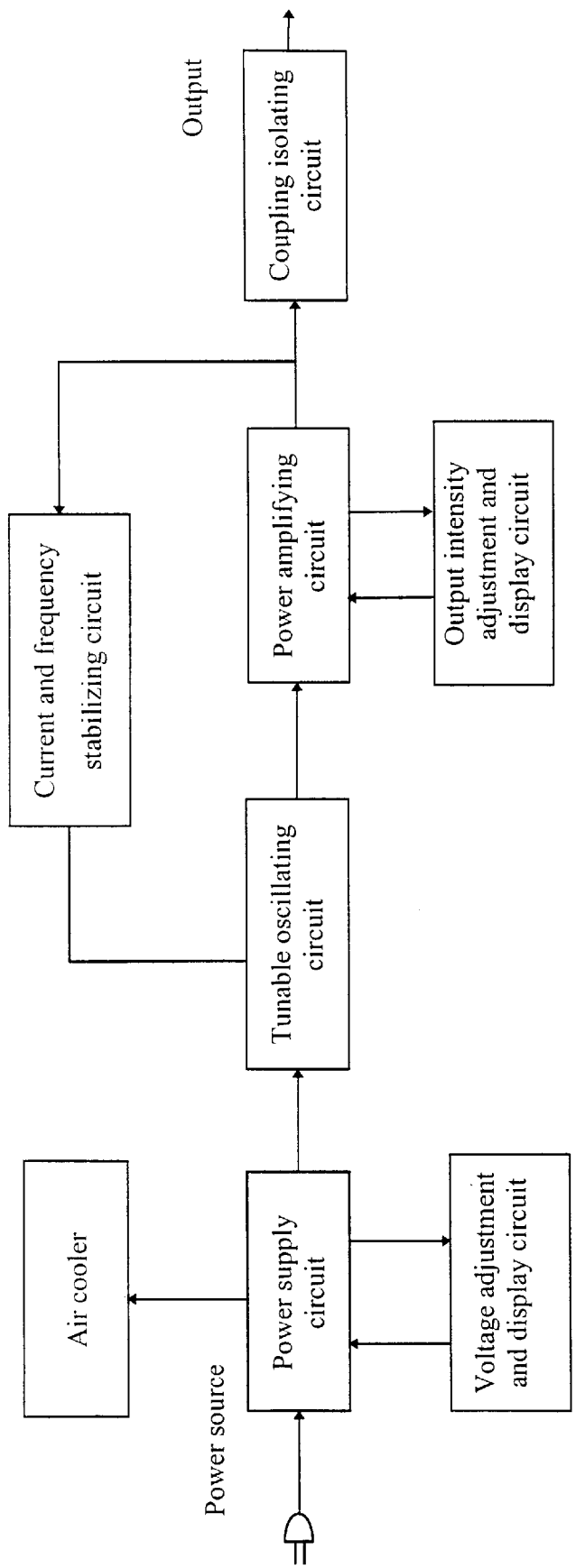
FIG. 1 is a block diagram showing the circuitry of a signal source of the ultra-high-frequency cosmetic apparatus according to the present invention.
Figure 2:
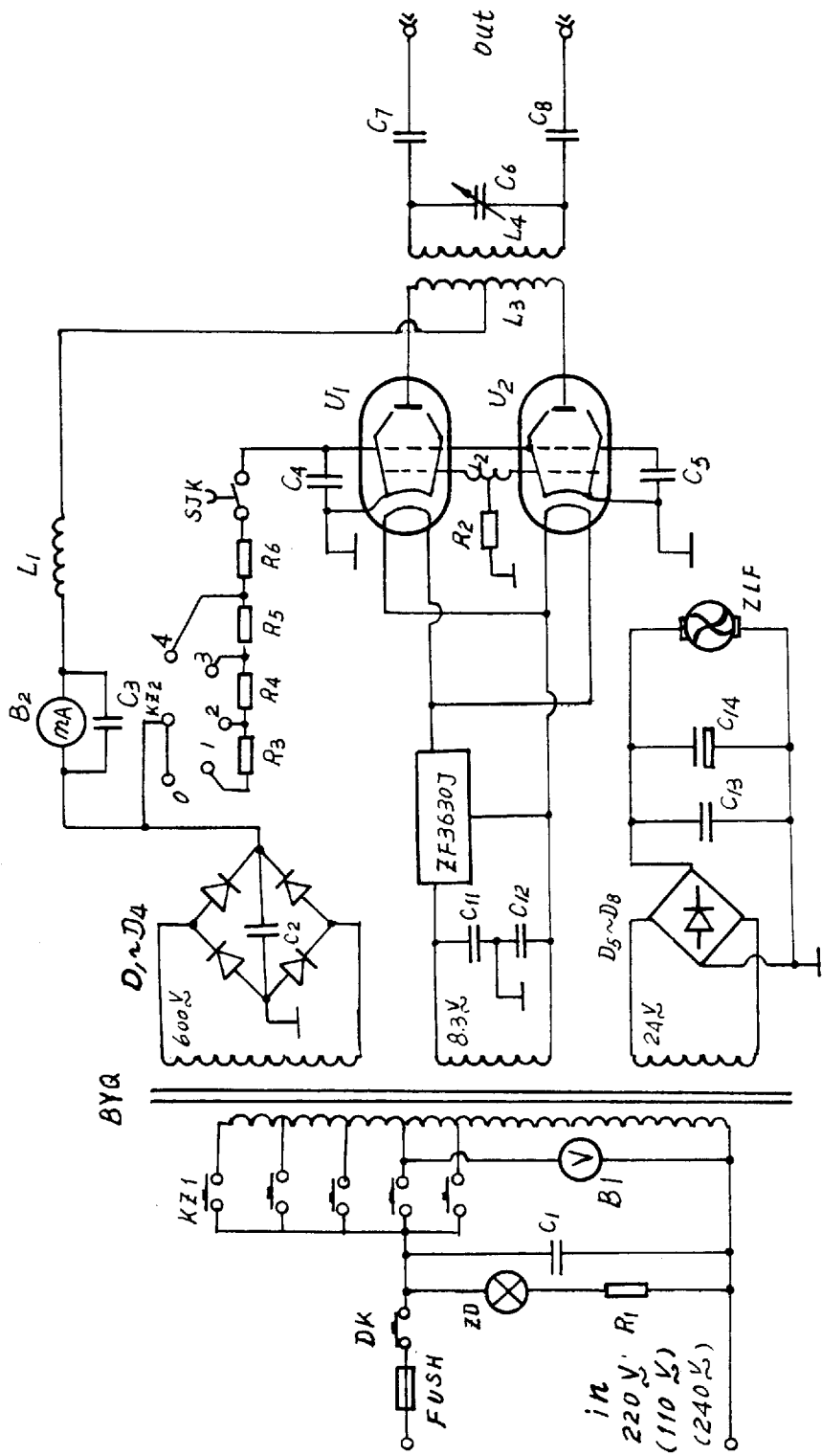
FIG. 2 is a schematic diagram of the circuitry of an embodiment of the present invention.

The ultra-high-frequency cosmetic apparatus proposed by the present invention comprises an ultra-high-frequency signal source and electrodes used therewith. Considering that the improvement of the present invention put emphasis upon the signal source and that the electrodes and electric blades have already been described in detail in Chinese patent application No.91104006, only the signal source will be described in detail in the following. Referring to FIGS. 1 and 2, the signal source circuit of the ultra-high-frequency cosmetic apparatus according to the present invention comprises, in turn, a power supply circuit section, a tunable oscillating circuit section, a power amplifying circuit section and a coupling isolating circuit section, as well as a current and frequency stabilizing circuit section.

The following is a detailed description of each of the circuit sections:

1. Power supply circuit: it employs self-compensating adjustment design which enables compensation for the fluctuations of the power supply voltage within the range of −15%−+10%, thus making the present invention applicable directly in areas of poor electric network conditions without the need of additional AC stabilizer. In addition to the functions such as voltage adjustment and display, switch indication, excess current protection and etc., the power supply circuit mainly supplies three voltages to the whole device: 600 V as anode voltage of the electronic tubes in subsequent circuit sections, 6.3 V as filament voltage of the electronic tubes and 24 V as voltage of an air cooler.

As shown in FIGS. 1 and 2, DK, ZD, R1 constitute a power switch and indication circuit; C1, C2, C11, C12 and C13 are high-frequency shunt capacitors for resisting high-frequency interference; KZ1, BYQ, B1 constitute a power supply and voltage adjustment and display circuit; and D1–D4 constitute a rectification bridge for supplying Dc 600 V anode voltage to the electronic tubes.

2. Oscillating circuit and power amplifying circuit: it employs two electronic tubes which are power amplification beam-tetrods FU-7 (of course, it can also be replaced by high power triodes) in this embodiment and LC circuit to realize self-oscillation circuit to produce ultra-high-frequency signals which are output after push-pull power amplification. The whole circuitry has the functions of tuning, output intensity control and display. As shown in FIG. 2, a tunable, ultra-high-frequency oscillating, push-pull power amplifier is constituted by U1, U2, L1–L4, C4–C6 and R2–R6. L4 and C6 constitute a tuning loop which also serves as an output intensity fine controller. R3–R6 and KZ2 constitute a gate voltage regulating circuit which serves to implement graded adjustment of output intensity. B2 is a DC 200 mA current meter which serves to display output intensity. SJK is a time switch.

3. Coupling isolating circuit: it employs capacitive energy output scheme of inductive coupling and double capacitor isolating. Signals are output via the inductive coupling constituted by L3 and L4 and the capacitive isolating constituted by C7 and C8. Such circuitry design ensures safety for the direct application of naked metallic electrodes on the human body.

4. Current and frequency stabilizing circuit: as shown in FIG. 2, ZF3630J current stabilizer assembly is employed to control to some extent the frequency deviation fluctuation to improve system stability by the use of current stabilizing method of the cathode emitting current.

In addition, an air cooler can be provided in the signal source of the cosmetic apparatus according to the present invention. In this embodiment, the air cooler is a DC axial air cooler ZLF for use in small instruments. The air cooler ensures the continuous operation of the wholes circuitry for more than 12 hours with stable performance.

In addition to the above-mentioned sections, the signal source according to the present invention adopts a structure for isolating the high-frequency part from the low-frequency part, while all the components and wires of the high-frequency sections are prepared by surface silver plating process (plating layer H>0.1 mm) to reduce signal attenuation of the high-frequency path.

Further, the present invention provides another ultra-high-frequency signal source which is constituted by the following circuits: referring to FIG. 1, a tunable oscillating circuit for generating ultra-high-frequency oscillating signals; a power amplifying circuit connecting with an output intensity adjustment and display circuit, the input of said power amplifying circuit being connected to the output of said tunable oscillating circuit, a current and frequency stabilizing circuit having its input connected to the output of said power amplifying circuit and its output connected to said tunable oscillating circuit, a coupling isolating circuit having its input connected to the output of said power amplifying circuit and its output connected to said output electrodes and said variety of surgical treatment applicances; and a power supply circuit for providing electrical power to said circuits, the circuit connecting with a voltage adjustment and display circuit.

The terms and expressions which have been employed are used as terms of description and not of limitation, and there is no intention in the use of such terms and expressions of excluding any equivalents of the features shown and described or portions thereof; it being recognized that various modifications are possible within the scope of the invention After treatment by the use of the cosmetic apparatus according to the present invention, the skin becomes smooth and flat without any scar and infection, and the recovery period is short. The present invention is suitable for use in medical and beauty services.

What is claimed is:

1. An ultra-high-frequency cosmetic apparatus comprising:

an ultra-high-frequency signal source having output electrodes connected thereto and a surgical treatment appliance detachably connected to at least one of the output electrodes, wherein the ultra-high-frequency signal source comprises a tunable oscillating circuit for generating ultra-high-frequency oscillating signals, a power amplifying circuit connecting with an output intensity adjustment and display circuit, the input of said power amplifying circuit being connected to the output of said tunable oscillating circuit, a current and frequency stabilizing circuit having its input connected to the output of said power amplifying circuit and its output connected to said tunable oscillating circuit, a coupling isolating circuit having its output connected to the output electrodes and said surgical treatment appliance; and a power supply circuit for providing electrical power to said circuit sections, which is connected with a voltage adjustment and display circuit; and the output signal of the apparatus has a frequency of 50–58 MHz and an intensity of 0–180 mA.

2. The ultra-high-frequency cosmetic apparatus of claim 1 wherein the output signal of said ultra-high-frequency cosmetic apparatus has a frequency of 50 MHz.

3. The ultra-high-frequency cosmetic apparatus of claim 2, wherein said appliance is selected from the group consisting of a needle and a blade.

4. The ultra-high-frequency cosmetic apparatus of claim 1 wherein the ultra-high-frequency amplifying circuit uses FU-7 electronic tubes and an LC self-excited oscillating circuit.

5. The ultra-high-frequency cosmetic apparatus of claim 4, wherein said appliance is selected from the group consisting of a needle and a blade.

6. The ultra-high-frequency cosmetic apparatus of claim 1 wherein the power amplifying circuit employs a push-pull amplifying circuit comprising a pair of FU-7 tubes.

7. The ultra-high-frequency cosmetic apparatus of claim 6, wherein said appliance is selected from the group consisting of a needle and a blade.

8. The ultra-high-frequency cosmetic apparatus of claim 1 wherein the coupling isolating circuit employs two capacitors having a resistance to voltage of more than 1 KV as isolating elements.

9. The ultra-high-frequency cosmetic apparatus of claim 8, wherein said appliance is selected from the group consisting of a needle and a blade.

10. The ultra-high-frequency cosmetic apparatus of claim 1 wherein the ultra-high-frequency cosmetic apparatus is provided with cooling means.

11. The ultra-high-frequency cosmetic apparatus of claim 10 wherein the cooling means is an air cooler.

12. The ultra-high-frequency cosmetic apparatus of claim 10, wherein said appliance is selected from the group consisting of a needle and a blade.

13. The ultra-high-frequency cosmetic apparatus of claim 1, wherein said appliance is selected from the group consisting of a needle and a blade.

14. An ultra-high-frequency cosmetic apparatus comprising:

an ultra-high-frequency signal source, output electrodes and a variety of surgical treatment appliances in the forms of needle and blade, wherein the ultra-high-frequency signal source comprises a tunable oscillating and power amplifying circuit for generating ultra-high-frequency oscillating signals, the circuit connecting with an output intensity adjustment and display circuit and using a plurality of electronic tubes, a coupling isolating circuit having its input connected to the output of said tunable oscillating and power amplifying circuit and its output connected to said output electrodes and said variety of surgical treatment appliances; a power supply circuit for providing 600 V as anode voltage of said electrode tube, 8.3 V as filament voltage of said electronic tube, the circuit connecting with a voltage adjustment and display circuit, and a current and frequency circuit having its input connected to the output of 8.3 V of said power supply circuit and its output connected to the filaments of the electronic tubes of said tunable oscillating and power amplifying circuit; and the output signal of the apparatus has a frequency of 50–58 MHz and an intensity of 0–180 mA.

15. The ultra-high-frequency cosmetic apparatus of claim 14 wherein the output signal of said ultra-high-frequency cosmetic apparatus has a frequency of 50 MHz.

16. The ultra-high-frequency cosmetic apparatus of claim 14 wherein the ultra-high-frequency oscillating circuit uses FU-7 electronic tubes and an LC self-excited oscillating circuit.

17. The ultra-high-frequency cosmetic apparatus of claim 14 wherein the power amplifying circuit employs a push-pull power amplifying circuit consisting of a pair FU-7 tubes.

18. The ultra-high-frequency cosmetic apparatus of claim 14 wherein the coupling isolating circuit employs two capacitors having a resistance to voltage of more than 1 KV as isolating elements.

19. The ultra-high-frequency cosmetic apparatus of claim 14 wherein the ultra-high-frequency cosmetic apparatus is provided with cooling means.

20. The ultra-high-frequency cosmetic apparatus of claim 19 wherein the cooling means is an air cooler.

* * * * *

UNITED STATES PATENT AND TRADEMARK OFFICE
CERTIFICATE OF CORRECTION

PATENT NO : 5,833,686
DATED : November 10, 1998
INVENTOR(S): Zhao

It is certified that error appears in the above-identified patent and that said Letters Patent is hereby corrected as shown below:

In Column 3, line 35, change "Dc" to --DC--.

In Column 4, lines 29-40, the paragraph beginning "After treatment..." and ending "... beauty services." (lines 36-40) should be moved to line 20 so that it precedes the paragraph beginning "The terms..." and ending "...the invention." (Lines 29-35).

In claim 14, column 6, line 12, before "circuit" add --stabilizing--.

Signed and Sealed this

First Day of June, 1999

Attest:

Attesting Officer

Q. TODD DICKINSON

Acting Commissioner of Patents and Trademarks